US00PP15797P2

(12) United States Plant Patent
Olesen et al.

(10) Patent No.: US PP15,797 P2
(45) Date of Patent: Jun. 14, 2005

(54) ***CLEMATIS* VARIETY 'EVIPO002'**

(50) Latin Name: *Clematis viticella*
Varietal Denomination: EVIpo002

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 13 days.

(21) Appl. No.: 10/644,620

(22) Filed: Aug. 19, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a compact growth habit and profuse, Red-Purple flowers which have good color retention. The variety successfully propagates from softwood cuttings and is suitable for cultivation in commercial glasshouses. This new and distinct variety has shown to be uniform and stable in the resulting generations from asexual propagation.

1 Drawing Sheet

Botanical classification: *Clematis viticella.*
Variety denomination: 'EVIpo002'.
Commercial classification: Early-large flowering cultivar.

SUMMARY OF THE DISCOVERY

The present discovery constitutes a new and distinct variety of *Clematis* which originated from an uncontrolled pollination of two unknown *Clematis* plants. The claimed plant was discovered in a cultivated area. The new variety is named 'EVIpo002'.

The objective of the selection of this *Clematis* variety for commercial glasshouse and nursery culture was to create a new and distinct variety with unique qualities such as:

1. Large full form red-purple flowers.
2. Compact Growth.
3. Yellow flower center.
4. Strong flower color with good color retention.

These qualities required improvement in *Clematis* varieties that were in commercial cultivation and the objectives have been substantially achieved in the new variety, as evidenced by the unique combination of characteristics that are present in 'EVIpo002' which distinguish it from all other varieties of which we are aware.

Evaluations were conducted on the discovered seeling in a controlled environment. 'EVIpo002' was selected by Raymond J. Evison and Mogens N. Olesen in their *Clematis* development program in Domarie Vineries Les Sauvagees, St. Sampsons, Guernsey, Channel Islands, United Kingdom in April 1997.

Asexual reproduction of 'EVIpo002' by cuttings was first done by Raymond J. Evison and Mogens N. Olesen in Domarie Vineries Les Sauvagees, St. Sampsons, Guernsey, Channel Islands, United Kingdom in May 1997. This initial and subsequent propagations have demonstrated that the characteristics of 'EVIpo002' are true to type and are transmitted from one generation to the next.

BRIEF DESCRIPTION OF THE DRAWING

The accompanying color illustration show as true as is reasonably possible to obtain in color photographs of this type:

FIG. 1.1 Juvenile foliage attached to stems, petiole, petiolule, and stems;

FIG. 1.2 Mature foliage with petiole;

FIG. 1.3 Bracts and various stages of flower development;

FIG. 1.4 Open flower, upper side

FIG. 1.5 Open flower, lower side

DETAILED DESCRIPTION OF THE VARIETY

The following is a detailed description of 'EVIpo002', as observed in its growth throughout the flowering period in glasshouses at Domarie Vineries Les Sauvagees, St. Sampsons, Guernsey, Channel Islands, United Kingdom. Plants were cultivated for two years in two liter pots. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Niobe', a non-patented variety. Chart 1 details several physical characteristics of the claimed *Clematis* plant and the comparison variety.

CHART 1

| | 'EVIpo002' | 'Niobe' |
|---|---|---|
| Leaflet size | 40 to 50 mm | 30 to 40 mm |
| Tepal width | 30 to 40 mm | 25 to 30 mm |
| Flower diameter | 120 to 180 mm | 100 to 150 mm |
| Tepal overlap | Tepals overlap by 5 to 10 mm | Tepals do not normally overlap |

FLOWER AND FLOWER BUD

Blooming habit: Normally blooms in April, May, and June recurring in August, September, and October. Flowering may be prolonged throughout the growing season if pruned accordingly.

Flower bud:

*Size.*—30 to 40 mm in length. 10 to 13 mm in diameter.

*Bud form.*—Long ovoid.

*Bud color.*—Red Purple Group 61A at ¼ opening.

*Tepals.*—Purple Group N79C.

*Peduncle.*—Surface: Smooth. Length: 90 to 120 mm average length. Color: Green Group 131A. Strength: Strong. Diameter: 2 mm.

*Borne.*—Normally compound cymes. Early season flowers may be borne single.

Flower bloom:

*Size.*—120 to 180 mm in diameter.

*Form.*—Upon opening: Flat with tepals slightly reflexing.

*Depth.*—Flower depth as viewed from the side is 5 to 10 mm. Reproductive parts protrude giving flower overall depth of 15 to 20 mm.

*Tepal color.*—Upon opening; Upper Surface is Red-Purple Group 71A. Lower Surface is Red-Purple Group 71A. After opening; Upper Surface is Red-Purple Group 71A. Lower Surface is Red-Purple is Purple N79C. At the basal zone, tepals are Violet N90A.

*Variations.*—As the flower matures, the upper surface of the tepal exhibits more blue tones and tends towards Purple RHS79C.

*Fragrance.*—None to very light floral fragrance.

*Lasting quality on plant and as a cut flower.*— 2 to 5 days as a cut flower. Flowers persist 7 to 12 days on the plant.

Tepals:

*Tepal count.*—Single Average: 6.

*Shape.*—Obovate. Base is obtuse. Apex is mucronate.

*Size.*—Normally 70 to 80 mm long by 30 to 38 mm wide.

*Cross section.*—Reflexed.

*Undulation of margin.*—Sepal margin is entire with slight undulations, 1 to 2 in quantity, along the length of the tepal. The depth of these undulations is typically 5 to 10 mm.

*Tepal apex.*—Cuspidate.

*Recurvature of tip.*—Slight.

*Persistence.*—Tepals drop off cleanly.

*Arrangement.*—Tepals are arranged regularly.

Reproductive organs:

*Pollen.*—Quantity: Average. Color: Yellow Group 11B.

*Anthers.*—Length: 4 to 7 mm. Color: Yellow Group 11B. Arrangement: Regular.

*Filaments.*—Color: White Group 155A.

*Pistil.*—Quantity: 30 to 45.

*Stigmas.*—Protrude from flower as it reaches full maturity.

*Styles.*—Yellow Group 11B.

*Seed production.*—Under normal conditions, each ovary will produce 15 to 25 seeds. Seed is Green Group 143C in color and is circular to tear shaped. Seed diameter is 2 to 3 mm with an elongated plumule 15 to 25 mm in length.

PLANT

Plant form: Climbing and spreading.

Plant growth: Moderately vigorous.

Height: Seasons growth attains 2 to 2.5 meters.

Width: 1 to 2 meters.

Hardiness: Trials to date show the variety hardy in USDA Zones 4–9.

Stems:

*Color.*—Young wood: Red Purple Group 61A. Older wood: Greyed Orange Group 165C.

*Internodes.*—Cylindrical. Length: 180 to 120 mm.

*Dimensions.*—Normally 1 to 2 meters in length. Diameter is 2 to 3 mm on average.

*Petioles.*—Size: Average length: 60 to 80 mm. Color: Red Purple 61A. Undersurface: Smooth. Clasping: By leaf Petiole.

*Bark.*—Young wood: Smooth. Older wood: Smooth.

Plant foliage: Deciduous.

*Form.*—Three broadly ovate leaflets arranged in pinnate form.

*Terminal leaflet size.*—40 to 50 mm in length by 70 to 80 mm wide.

*Compound leaf size.*—On average, 120 mm long by 100 mm wide.

*Abundance.*—Above Average.

*Color.*—Above: Green Group 137B. Bottom: Green Group 137B.

Plant leaves and leaflets:

*Stipules.*—Absent.

*Petioloule.*—Length: 10 to 30 mm. Color: Red Purple 61A.

*Leaf edge.*—Terminal leaflet margin is entire with mild undulations.

*Shape.*—Base of leaflet: Rounded to Cordate. Apex of leaflet: Acute.

*Texture.*—Upper side: Rough. Lower side: Rough.

*Thickness.*—Moderate.

*Glossiness.*—Matte Finish.

Disease resistance: Subject to any disease that normally attacks the species, however the variety is more tolerant to *Botrytis* and mildew than some *Clematis*.

It is claimed:

1. A new and distinct variety of *Clematis* plant named 'EVIpo002', as illustrated and described herein as a distinct and novel *Clematis* variety due to its compact growth habit and profuse, Red-Purple flowers which have good color retention, year round flowering under glasshouse conditions, suitability for production from softwood cuttings in pots, durable flowers and foliage which make the variety suitable for distribution in the floral industry.

* * * * *

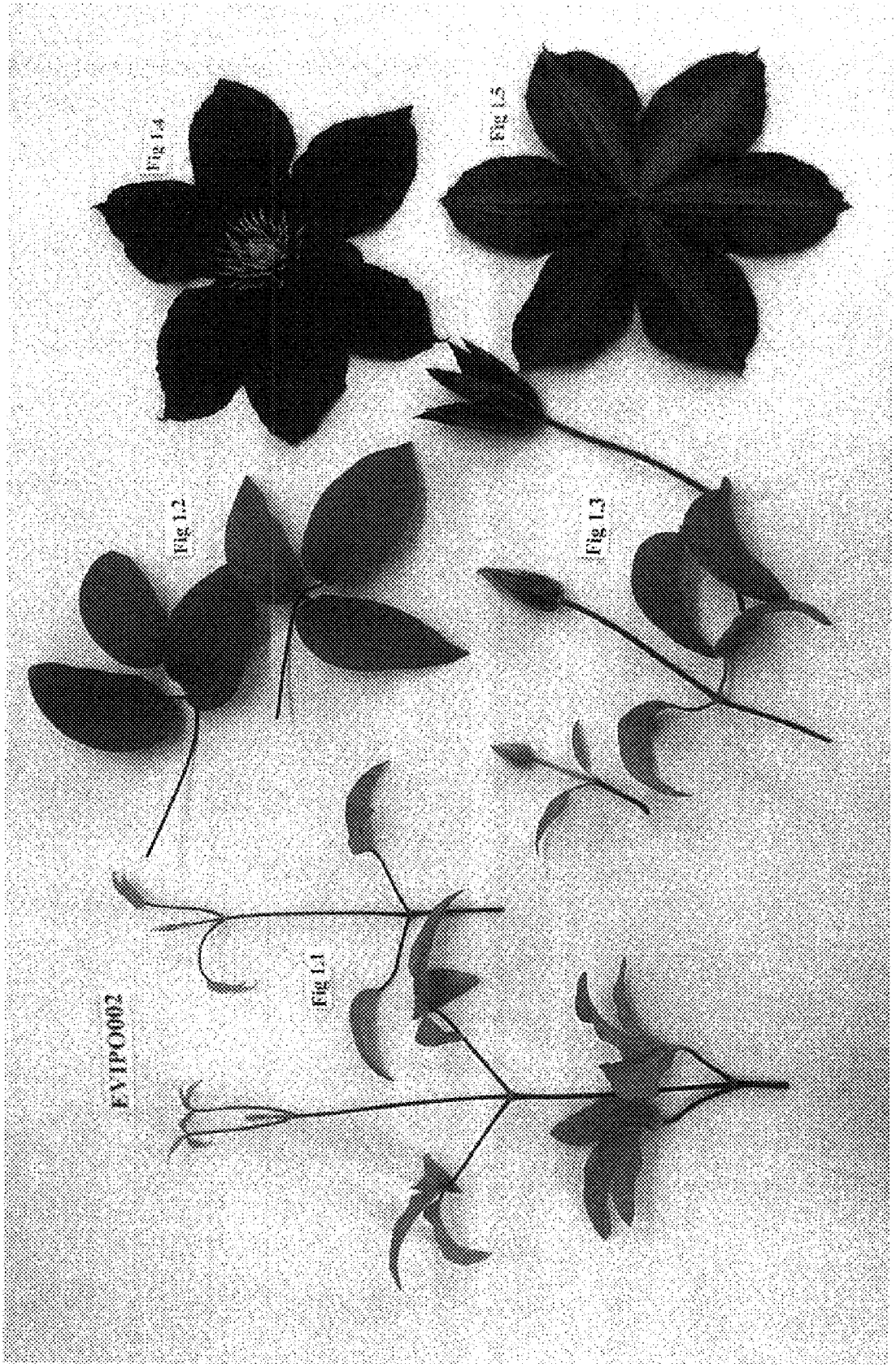
EYTPO002
Fig 1.1
Fig 1.2
Fig 1.3
Fig 1.4
Fig 1.5